United States Patent
Krantz

[11] 3,971,378
[45] July 27, 1976

[54] EXPANSIBLE TAMPON

[75] Inventor: Kermit E. Krantz, Shawnee Mission, Kans.

[73] Assignee: Ortho Pharmaceutical Corporation, Raritan, N.J.

[22] Filed: Dec. 20, 1974

[21] Appl. No.: 534,758

[52] U.S. Cl. .............................. 128/285
[51] Int. Cl.² .............................. A61F 13/20
[58] Field of Search ........... 128/285, 286, 294, 270, 128/271

[56] References Cited
UNITED STATES PATENTS

| | | | |
|---|---|---|---|
| 61,417 | 1/1867 | Grant | 128/285 |
| 3,079,921 | 3/1963 | Brecht et al. | 128/285 |
| 3,431,909 | 3/1969 | Krusko | 128/285 |
| 3,610,243 | 10/1971 | Jones | 128/285 |
| 3,618,605 | 11/1971 | Glassman | 128/285 |
| 3,706,311 | 12/1972 | Kokx et al. | 128/285 |
| 3,731,687 | 5/1973 | Glassman | 128/285 |
| 3,762,413 | 10/1973 | Hanke | 128/285 |

Primary Examiner—Lawrence W. Trapp
Attorney, Agent, or Firm—Dressler, Goldsmith, Clement & Gordon, Ltd.

[57] ABSTRACT

A tampon which is expansible in the vagina, once inserted, for improved absorbence of menstrual fluid, particularly in post-partum women. The tampon includes an absorbent member and a core embedded within the absorbent member and constructed to expand the absorbent member so that it closely conforms to the shape of the vaginal wall. Initially, the absorbent member and core are compressed and snugly positioned within a tubular applicator which is used to guide the insertion of the tampon into the vagina. In the compressed position, the lateral extent of the leading end of the absorbent member, the end thereof to be positioned adjacent the cervix, is approximately the same as the lateral extent of the opposite end of the absorbent member. Once the tampon is discharged from the applicator, the core expands the absorbent member from the compressed position to a relaxed position where the end of the absorbent member nearest the cervix is wider than the end of the absorbent member facing the exterior of the vagina.

29 Claims, 8 Drawing Figures

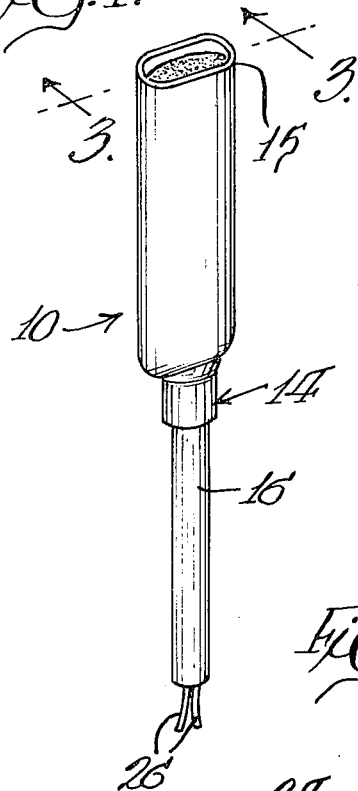
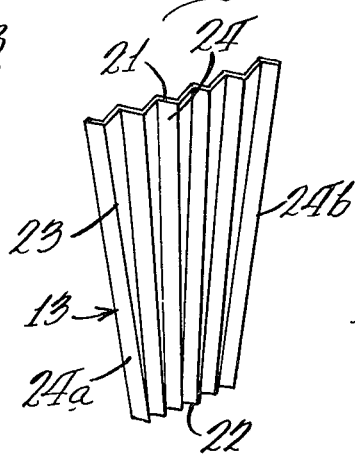
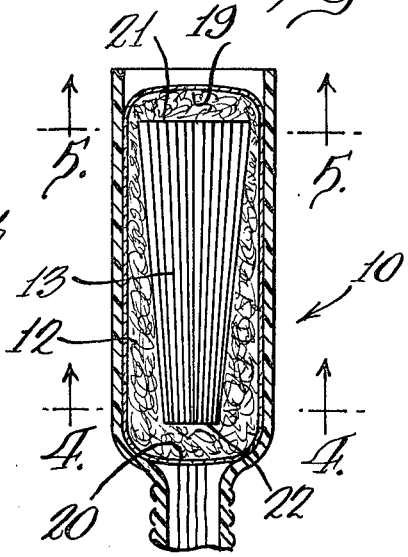
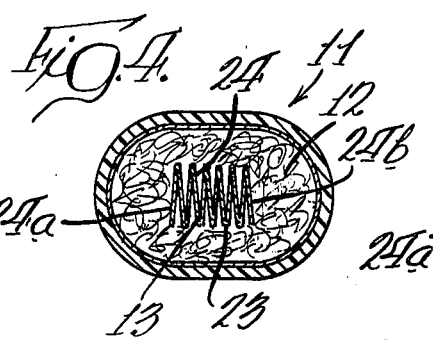
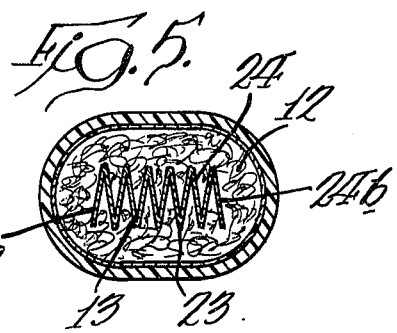
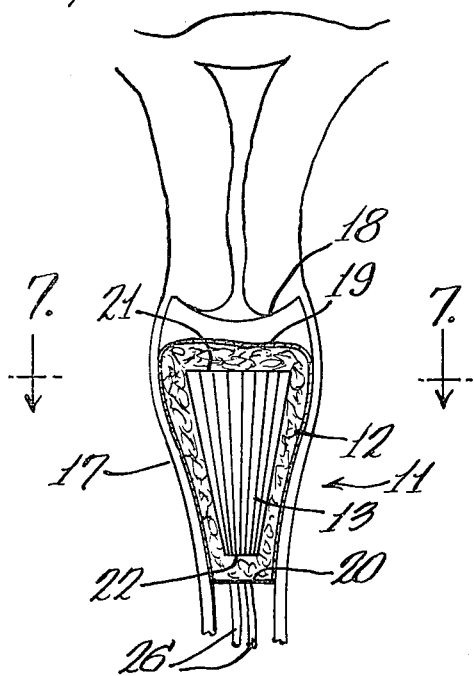
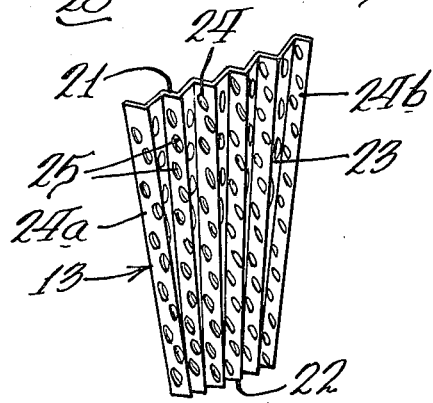

EXPANSIBLE TAMPON

BACKGROUND OF THE INVENTION

Tampons have proven to be safe and effective devices for use in absorbing menstrual fluid. A conventional tampon consists of an elongated cylindrical member of compressed absorbent material which fits within a tubular applicator that is used to insert the tampon into the vagina. After insertion into the vagina, any expansion which occurs is generally uniform from one end of the tampon to the opposite end, so that the tampon maintains a cylindrical configuration.

There are several problems with conventional tampons. The absorbent member is often so greatly compressed that menstrual fluid quickly saturates the end of the tampon closest to the cervix and the exterior surface of the tampon, while the interior of the tampon remains relatively free of menstrual fluid. Menstrual fluid is thereby permitted to bypass the saturated tampon and escape through the vagina. Conventional tampons are also inadequate during periods of heavy flow, and it is common for a woman to wear a sanitary napkin in addition to the tampon during such periods.

A problem that is particularly acute with post-partum women is that very often the vagina becomes distored resulting in increased surface area, lateral gutters with a large number of folds, and an open cervix. The conventional generally cylindrical tampon is inherently incapable of conforming to such an anatomical configuration, and hence provides inadequate absorbent characteristics. Commercially available tampons are also inadequate in situations when other distortions of the anatomy take place, such as herniations of the bladder and rectum which cause distortions in the wall of the vagina.

SUMMARY OF THE INVENTION

The tampon of the present invention solves the problems set forth above by virtue of a structure which is expansible within the vagina so as to accommodate anatomical distortions thereof. The tampon includes an elongated absorbent member, preferably formed of cellulosic material, and a spreader means for causing the absorbent member to expand and conform to the shape of the vagina once it is inserted.

In the presently preferred embodiment of the invention, the spreader means is provided by an inherently expansible plastic core which is embedded in the center of the absorbent member, and which has sufficient elastic memory to cause the leading end of the absorbent member facing the woman's cervix to be wider than the trailing end of the absorbent member once the tampon is in place and the core is relaxed. Both the absorbent member and the applicator tube by which the tampon is inserted are oval in cross section to aid the woman in properly aligning the tampon so that once the core expands, the sides of the absorbent member will be spread outwardly into the lateral gutters of the vagina.

Unlike conventional tampons which expand primarily through the absorption of fluids, the tampon of the present invention expands to a relaxed position immediately after the insertion into the vagina, thereby expanding the absorbent member prior of the absorption of liquids. The expansion of the tampon maximizes the surface area available to absorb fluids and therefore permits quick absorption of large amounts of fluids, as compared to conventional tampons which are greatly compressed and become quickly saturated at the end closest to the cervix and along the exterior surface. Other advantages will become apparent from the reading of the following detailed description.

BRIEF DESCRIPTION OF THE DRAWINGS

FIG. 1 is a perspective view of the tampon in an applicator;

FIG. 2 is a perspective view of the core of the tampon in FIG. 1, and illustrating the core in the expanded position it assumes when in place in the vagina;

FIG. 3 is an enlarged cross-sectional view taken along plane 3—3 in FIG. 1;

FIG. 4 is a cross-sectional view taken along plane 4—4 in FIG. 3;

FIG. 5 is a cross-sectional view taken along plane 5—5 in FIG. 3;

FIG. 6 is a cross-sectional view of the tampon shown in FIG. 1, illustrating the tampon in its relaxed position in the vagina;

FIG. 7 is a cross-sectional view taken along plane 7—7 in FIG. 6; and

FIG. 8 is an enlarged perspective view showing an alternate embodiment of the core.

DETAILED DESCRIPTION OF THE PREFERRED EMBODIMENT

While this invention is susceptible of embodiments in many different forms, there are shown in the drawings and will herein be described in detail, preferred embodiments of the present invention, with the understanding that the present disclosure is to be considered as an exemplification of the principles of the invention and is not intended to limit the invention to the embodiments illustrated. The scope of the invention will be pointed out in the appended claims.

Referring now to the drawings, the tampon-applicator combination of the present invention is illustrated in its entirety at 10 in FIGS. 1 and 3, and is comprised of a tampon 11 removably positioned within a tubular applicator 14. Tampon 11 includes an absorbent member 12 having an expansible core 13 embedded in the center thereof. Applicator 14 has an open end 15 and a slidable plunger 16 at the opposite end, for shifting the tampon axially of the applicator to insert the tampon in a vagina 17 and adjacent cervix 18 (FIG. 6). Applicator 14 has an oval cross-sectional shape, and the inner wall thereof snugly embraces the absorbent member.

Absorbent member 12 is axially elongated and has a leading end 19 disposed in close proximity to the cervix 18 once the tampon is inserted, and an opposite or trailing end 20 that is engaged by the end of plunger 16 when the tampon is being inserted. In the compressed position within applicator 14 the absorbent member has an oval or elliptical cross-sectional shape, and the lateral extent of the absorbent member is approximately equal at free end 19, opposite end 20, and all points therebetween. The absorbent member may be formed of any conventionally used absorbent material such as cotton, rayon, or cellulose, and the absorbent material is preferably initially slightly compressed.

Core 13 is also axially elongated and completely surrounded by absorbent member 12. A first end 21 of core 13 faces toward the free or leading end 19 of the absorbent member and a second end 22 of the core faces toward the opposite end 20 of the absorbent member. Core 13 is formed of a material having an inherent elastic memory, and in the compressed position (FIGS. 3–5), and in the expanded or relaxed position (FIG. 2), end 22 is narrower than end 21. However, in the relaxed position end 21 expands to assume a significantly increased lateral dimension (as compared to the lateral dimension in the compressed position) while the lateral dimension of end 22 stays essentially the same in both the compressed and relaxed positions. Core 13 is preferably formed of a rigid, flexible non-absorbent material, although it is recognized that certain inherently expansible absorbent materials may also be suitable. The core may be a polymer, (such as polyethylene, nylon, etc.), or a metal (such as stainless steel, aluminum, etc.) that is insoluble in body fluids and tissues and non-reactive with them.

In the disclosed embodiments, core 13 is an accordion member including flat outer side portions 24a and 24b and intermediate flat portions 24 connected to one another by folds 23. The present invention contemplates that the core may take other forms different than that illustrated, so long as the core is effective to spread the leading end of the absorbent member once the tampon is inserted into the vagina. The core is preferably uniformly tapered from the leading end to the trailing end in both the compressed and the relaxed positions to in effect form an inverted truncated cone, although this is not critical to the present invention. To promote flow of fluids through the core, a plurality of perforations 25 may be provided in the core as in the embodiment illustrated in FIG. 8. Alternatively, the core may be a crimped mesh or screen-like member. Other crimped, fluted or coiled constructions employing an inherently expansible core will occur to those skilled in the art.

The structure may, if desired, be an integral structure in which the spreader means and the absorbent means are combined. One example of such a structure would be a porous material, such as a uniform blend of cellulose fibers and cellulose acetate fibers, which is molded into the desired shape and then compressed. In such a structure, the thermoplastic cellulose acetate fibers provide the desired moldability; and the cellulose fibers provide the desired absorbency.

Alternatively, cellulose fibers and cellulose acetate fibers may be combined in a layered structure with the interior spreader means comprising all, or primarily, cellulose acetate fibers while the exterior absorbent means comprises all, or primarily, cellulose fibers. In this embodiment, there may be a sharp interface between two distinct layers; or there may be a gradual transition in the relative concentrations of the fibers going outwardly from the center.

In still another embodiment, a preformed porous spreader means may be dipped into a slurry, or suspension, of pulp fibers and the fibers are then drawn to the surface of the spreader means by the application of suction thereto after which the unit is dried.

Alternatively, absorbent material may be molded directly onto or dispersed throughout the core, or the core may comprise a porous material which can be molded into the desired shape and then compressed. For example, the tampon may be formed of a cellulosic, single casted material wherein the core is molded from a double layered material, such as cotton, that contains a webbing to maintain the expanded shape.

Strings 26 are connected to both the absorbent member 12 and to the core 13 for removal of the tampon, and removal is facilitated by the tapered configuration.

The tampon can be formed in different sizes to accommodate various needs, such as variations in flow rates between different users. For example, the tampon may have a length of 5 cm. between free end 19 and 20 of absorbent member 12, a lateral extent of 1 cm. along the entire the length in the compressed position, and a lateral extent in the relaxed position of 4 cm. across free end 19 of absorbent member 12 and 1 cm. across opposite end 20 of absorbent member 12. The tampon may also be formed in a larger size having a length of 5 cm. between free end 19 and opposite end 20 of absorbent member 12, a lateral extent of 1 cm. along the entire length in the compressed position, and a lateral extent in the relaxed position of 6 cm. across free end 19 and opposite end 20 of absorbent member 12, and a lateral extent in the relaxed position of 6 cm. across free end 19 of absorbent member 12 and 1.5 cm. across opposite end 20 of absorbent member 12. The length of the tampon between the free and opposite ends of the absorbent member is preferably between 4 cm. and 7 cm., although shorter and longer sizes may also be suitable. Likewise, the lateral extent of the tampon may be shorter, longer, or between the dimensions herein discussed as examples. The sizes herein discussed are examples only, and are not meant to limit the invention to these specific configurations.

In use, the open end 15 of the applicator 14 is inserted at least one half cm. inside the vagina and plunger 16 is moved forwardly to discharge the tampon into the vagina. The tampon is positioned in close proximity to the cervix as is clear from FIG. 6. After the applicator has been removed, the core 13 immediately and rapidly expands thereby causing a corresponding expansion in absorbent member 12, and causing the absorbent member to extend to the lateral gutters at the sides of the vagina, as is evident from FIGS. 6 and 7. As can also be seen from FIG. 7, the absorbent member 12 retains its general oval cross-sectional shape in the relaxed position. The spreading action effected by core 13 causes the absorbent member to closely conform to the shape of the wall of the vagina and maximizes the exposed surface area of absorbent material. The absorbent material is preferably applied to the core prior to the compression thereof so that it will expand with the core in the vagina and not tear or rupture.

It should be noted that while the primary utility of the present invention is as a tampon, it may also be used to deliver and hold therapeutic medication (either systemic and/or local) high in the lateral gutters of the vagina. Devices formed in accordance with the present invention may also be utilized to deliver drugs to control fertility.

I claim:

1. A tampon comprising: an axially elongated, unitary absorbent member adapted to be inserted into the vagina with the leading end facing the cervix and disposed in close proximity thereto and the trailing end facing the exterior of the vagina, said trailing end being disposed in axial alignment with said leading end, axially elongated spreader means disposed within and surrounded by said unitary absorbent member for expanding said absorbent member from a compressed position for insertion of the tampon into the vagina to a relaxed position which is assumed after insertion of the tampon into the vagina, said spreader means having a leading end facing the leading end of the absorbent member and a trailing end facing the trailing end of the absorbent member, the trailing end of the spreader means being disposed in axial alignment with the leading end thereof, the lateral extent of the leading end of the absorbent member being approximately equal to the lateral extent of the trailing end of the absorbent member in the compressed position, and the lateral extent of the leading end of the absorbent member being larger than the lateral extent of the trailing end of the absorbent member in the relaxed position, said tampon adapted to expand and conform to the shape of the most distensible portion of the vagina upon insertion of said tampon therein, said tampon being sufficiently absorbent so as to be adapted for use in a post partum woman.

2. A tampon as claimed in claim 1 wherein said absorbent member is comprised of a cellulosic material.

3. A tampon as claimed in claim 1 wherein said absorbent member has an oval cross-sectional shape.

4. A tampon as claimed in claim 3 wherein said core is formed of a non-absorbent material.

5. A tampon as claimed in claim 1 wherein said spreader means is a core embedded within the center of said absorbent member.

6. A tampon as claimed in claim 5 wherein said core contains a plurality of voids to facilitate passage of fluids being absorbed.

7. A tampon as claimed in claim 5 wherein said core is formed of a polymeric material.

8. A tampon as claimed in claim 7 wherein said material is polyethylene.

9. A tampon as claimed in claim 5 wherein a string is attached to both said absorbent member and said core to facilitate removal of said tampon after use.

10. A tampon as claimed in claim 5 wherein said absorbent member in said relaxed position is generally uniformly tapered between said leading end and said trailing end.

11. A tampon as claimed in claim 5 wherein said core extends generally from end to end of said absorbent member, the end of said core adjacent the leading end of said absorbent member being wider than the end of the core adjacent the trailing end of the absorbent member in both the compressed and relaxed positions. and 12. A tampon comprising a unitary absorbent member adapted to be inserted into the vagina with the leading end facing the cervix and disposed in close proximity thereto and the trailing end facing the exterior of the vagina, spreader means disposed within said unitary absorbent member for expanding said absorbent member from a compressed position for insertion of the tampon into the vagina to a relaxed position which is assumed after insertion of the tampon into the vagina, said spreader means being a core embedded within the center of said absorbent member, said core having a plurality of elongated generally flat portions longitudinally folded over upon themselves, the lateral extent of the leading end of the absorbent member being approximately equal to the lateral extent of the trailing end of the absorbent member in the compressed position, and the lateral extent of the leading end of the absorbent member being larger than the lateral extent of the trailing end of the absorbent member in the relaxed position, said tampon adapted to expand and conform to the shape of the most distensible portion of the vagina upon insertion of said tampon therein, said tampon being sufficiently absorbent so as to be adapted for use in a post partum woman.

13. The tampon of claim 12 wherein said absorbent member is comprised of a cellulosic material.

14. A tampon as claimed in claim 1 wherein said spreader means and absorbent member are unitary.

15. A tampon comprising: an axially elongated unitary absorbent member adapted to be inserted into the vagina with the leading end facing the cervix and disposed in close proximity thereto and the trailing end facing the exterior of the vagina, said trailing end being disposed in axial alignment with said leading end, said unitary absorbent member being generally oval in cross-sectional shape; axially elongated spreader means disposed within and surrounded by said unitary absorbent member for expanding said absorbent member from a compressed position for insertion of the tampon into the vagina to a relaxed position which is assumed after insertion of the tampon into the vagina, said spreader means having a leading end facing the leading end of the absorbent member and a trailing end facing the trailing end of the absorbent member, the trailing end of the spreader means being disposed in axial alignment with the leading end thereof, the lateral extent of the leading end of the absorbent member being approximately equal to the lateral extent of the trailing end of the absorbent member in the compressed position, and the lateral extent of the leading end of the absorbent member being larger than the lateral extent of the trailing end of the absorbent member in the relaxed position, said absorbent member tapering generally uniformly from said leading end to said trailing end in the relaxed position, said spreader means being defined by a core embedded within the center of said absorbent member and extending generally from end to end thereof, said core being formed of a material having an inherent elastic memory and being extensible to distend said absorbent member in the relaxed position, and means attached to both said absorbent member and said core for removing the tampon from the vagina, said tampon adapted to expand and conform to the shape of the most distensible portion of the vagina upon insertion of said tampon therein, said tampon being sufficiently absorbent so as to be adapted for use in a post partum woman.

16. In Combination: a tampon including an axially elongated unitary absorbent member adapted to be inserted into the vagina with the leading end facing the cervix and disposed in close proximity thereto and the trailing end facing the exterior of the vagina, said trailing end being disposed in axial alignment with said leading end, axially elongated spreader means disposed within and surrounded by said unitary absorbent member for expanding said absorbent member from a compressed position for insertion of the tampon into the vagina to a relaxed position which is assumed after insertion of the tampon into the vagina, said spreader means having a leading end facing the leading end of the absorbent member and a trailing end facing the trailing end of the absorbent member, the trailing end of the spreader means being disposed in axial alignment with the leading end thereof, the lateral extent of the leading end of the absorbent member being approximately equal to the lateral extent of the trailing end of the absorbent member in the compressed position, and the lateral extent of the leading end of the absorbent member being larger than the lateral extent of the trailing end of the absorbent member in the relaxed position; and an applicator for inserting the tampon into the vagina, said tampon adapted to expand and conform to the shape of the most distensible portion of the vagina upon insertion of said tampon therein, said tampon being sufficiently absorbent so as to be adapted for use in a post partum woman, said applicator including a tubular member having said tampon removably positioned therein, the wall of said tubular member retaining said core in said compressed position, said applicator further including a plunger mounted for movement axially of said tubular member and engageable with the trailing end of said absorbent member for discharging the tampon from the tubular member and into the vagina.

17. The combination of claim 16 wherein said tubular member is oval in cross section.

18. The combination of claim 17 wherein said absorbent member is oval in cross section in the compressed position.

19. In combination: a tampon including an axially elongated unitary absorbent member adapted to be inserted into the vagina with the leading end facing the cervix and disposed in close proximity thereto and the trailing end facing the exterior of the vagina, said trailing end being in axial alignment with said leading end, said unitary absorbent member being generally oval in cross-sectional shape, axially elongated spreader means disposed within and surrounded by said unitary absorbent member for expanding said absorbent member from a compressed position for insertion of the tampon into the vagina to a relaxed position which is assumed after insertion of the tampon into the vagina, said spreader means having a leading end facing the leading end of the absorbent member and a trailing end facing the trailing end of the absorbent member, the trailing end of the absorbent member being disposed in axial alignment with the leading end thereof, the lateral extent of the leading end of the absorbent member being approximately equal to the lateral extent of the trailing end of the absorbent member in the compressed position, and the lateral extent of the leading end of the absorbent member being larger than the lateral extent of the trailing end of the absorbent member in the relaxed position, said absorbent member tapering generally uniformly from said leading end to said trailing end in the relaxed position, said spreader means being defined by a core embedded within the center of said absorbent member and extending generally from end to end thereof, said core being formed of a material having an inherent elastic memory and being extensible to distend said absorbent member in the relaxed position, means attached to both said absorbent member and said core for removing the tampon from the vagina, said tampon adapted to expand and conform to the shape of the most distensible portion of the vagina upon insertion of said tampon therein, said tampon being sufficiently absorbent so as to be adapted for use in a post partum woman; and an applicator for inserting the tampon into the vagina, said applicator including a tubular member having said tampon removably positioned therein, the wall of said tubular member retaining said core in said compressed position, said applicator further including a plunger mounted for movement axially of said tubular member and engageable with the trailing end of said absorbent member for discharging the tampon from the tubular member and into the vagina.

20. The combination of claim 19 wherein said tubular member is oval in cross section.

21. The combination of claim 20 wherein said absorbent member is oval in cross section in the compressed position.

22. The tampon of claim 12 wherein said absorbent member has an oval cross-sectional shape.

23. The tampon of claim 12 wherein said core is formed of a non-absorbent material.

24. The tampon of claim 12 wherein said core contains a plurality of voids to facilitate passage of fluids being absorbed.

25. The tampon of claim 12 wherein said core is formed of a polymeric material.

26. The tampon of claim 25 wherein said material is polyurethane.

27. The tampon of claim 12 wherein a string is attached to both said absorbent member and said core to facilitate removal of said tampon after use.

28. The tampon of claim 12 wherein said absorbent member in said relaxed position is generally uniformly tapered between said leading end and said trailing end.

29. The tampon of claim 12 wherein said core extends generally from end to end of said absorbent member, the end of said core adjacent the leading end of said absorbent member being wider than the end of the core adjacent the trailing end of the absorbent member in both the compressed and relaxed positions.

* * * * *

UNITED STATES PATENT OFFICE
CERTIFICATE OF CORRECTION

Patent No. 3,971,378    Dated July 27, 1976

Inventor(s) Kermit E. Krantz

It is certified that error appears in the above-identified patent and that said Letters Patent are hereby corrected as shown below:

On the cover sheet, delete "[73] Assignee: Ortho Pharmaceutical Corporation, Raritan, N. J."

Signed and Sealed this

Eleventh Day of January 1977

[SEAL]

Attest:

RUTH C. MASON
*Attesting Officer*

C. MARSHALL DANN
*Commissioner of Patents and Trademarks*